United States Patent [19]

Ritter et al.

[11] Patent Number: 4,496,446

[45] Date of Patent: Jan. 29, 1985

[54] MODIFICATION OF POLYGLYCOLIC ACID STRUCTURAL ELEMENTS TO ACHIEVE VARIABLE IN-VIVO PHYSICAL PROPERTIES

[75] Inventors: Thomas A. Ritter, Bristol; Alan L. Kaganov, Stamford; John P. Budris, Cheshire, all of Conn.

[73] Assignee: American Cyanamid Company, Stamford, Conn.

[21] Appl. No.: 505,137

[22] Filed: Jun. 16, 1983

Related U.S. Application Data

[63] Continuation-in-part of Ser. No. 198,565, Oct. 20, 1980, abandoned, and a continuation-in-part of Ser. No. 198,566, Oct. 20, 1980, abandoned.

[51] Int. Cl.³ .................. C08G 63/70; C08J 3/28; C08J 7/10
[52] U.S. Cl. .................. 204/159.14; 264/22; 523/113; 523/114; 523/115; 3/1
[58] Field of Search .................. 204/159.14; 523/105, 523/113, 114, 115; 264/22

[56] References Cited

U.S. PATENT DOCUMENTS

| | | | |
|---|---|---|---|
| 2,964,455 | 12/1960 | Graham | 204/159.14 |
| 3,636,956 | 1/1972 | Schneider | 528/354 X |
| 3,867,190 | 2/1975 | Schmitt et al. | 427/2 |
| 3,991,766 | 11/1976 | Schmitt et al. | 128/335.5 |
| 4,135,622 | 1/1979 | Glick | 206/63.3 |
| 4,279,249 | 7/1981 | Vert et al. | 525/415 X |

FOREIGN PATENT DOCUMENTS

30822 6/1981 European Pat. Off. .
2742128 3/1978 Fed. Rep. of Germany .

OTHER PUBLICATIONS

Williams et al. and Chu et al., Ninth Annual Meet. Soc. for Biomaterials VI, 110 and 111 (4/1983).
Chu et al., J. of Biochemical Materials Resch. 16, 417-430 (7/1982).
Campbell et al., [Probably a Biomaterials Symposium], p. 66 (ca. 6-9/1981).

*Primary Examiner*—Earl A. Nielsen
*Attorney, Agent, or Firm*—A. R. Noe; Charles F. Costello, Jr.

[57] ABSTRACT

The physical properties of structural surgical elements which are made from bioabsorbable materials having a glycolic ester linkage can be controlled so that the rate of strength loss and degradation in vivo is altered to achieve disintegration into fragments suitable for removal from or passage through the body without the need for waiting until the material is absorbed. This is achieved by a method of modifying the element through various chemical and/or physical treatments, preferably irradiation, or combinations thereof, with the result that bioabsorbable structural surgical elements are made more controllable in their strength loss and degradation pattern.

3 Claims, No Drawings

MODIFICATION OF POLYGLYCOLIC ACID STRUCTURAL ELEMENTS TO ACHIEVE VARIABLE IN-VIVO PHYSICAL PROPERTIES

This is a continuation-in-part of application, Ser. Nos. 198,565 and 198,566, /filed Oct. 20, 1980, both abandoned.

FIELD OF THE INVENTION

This invention relates to structural surgical elements such as polyglycolic acid prostheses and, more particularly, to methods of achieving variable in vivo physical properties of such elements serving structural functions.

Prosthetic devices of polyglycolic acid having many useful medical applications are described in U.S. Pat. Nos. 3,620,218; 3,867,190 and 3,991,766. The surgical elements there disclosed take advantage of the fact that polyglycolic acid is bioabsorbable, that is, is digested or disolved in living mammalian tissue. It is stated that the rate of absorption as well as the short term strength requirements of the structural elements vary from patient to patient and at different locations within the body as well as with the mass of the polyglycolic acid element. In general, an absorbable prosthesis should have as high a portion of its original strength as possible for at least three days, and sometimes as much as 15 days or more, and preferrably should be completely absorbed by muscular tissue within from 45 to 90 days or more. One advantage or polyglycolic acid in a particular application disclosed in those patents is that it is completely dissolved in tissue and leaves minimal or no residual scar tissue.

Polylactide filaments and solid surgical acids are disclosed in U.S. Pat. No. 3,636,956. That patent states that the inherent viscosity of the polymer is lower following extrusion because some degradation of the polymer may occur. It is also stated that if sutures of the material are sterilized by high energy radiation, there may be a further lowering of the molecular weight and resulting decrease in tensile strength. Treatment with boiling water is said to cause the filaments to lose weight.

Prosthetic structures have been made from bicomponent materials. For example, U.S. Pat. No. 3,463,158 discloses a fabric of bicomponent fibers, of polyglycolic acid and Dacron ®. U.S. Pat. No. 4,192,021 discloses a prosthetic material consisting. of a mixture of calcium phosphates with biodegradable polymers. It is said that both the inorganic and organic constituents of the material are resorbable and gradually replaced by endogenic tissue and used as a bone replacement.

The surgical elements disclosed in the foregoing patents are intended to be absorbed by the body over a period of time. However, there are surgical elements the function of which is to serve as a temporary structural support but without gradual replacement or ingrowth by tissue and which are desirably removed from the surgical site after having fulfilled an initial support function. A typical example is a ring-like device useful for supporting sections of the colon to be anastomosed. Such a gastrointestinal or bowel anastomosis device is described and claimed in U.S. patent application Ser. No. 198,448, filed Oct. 20, 1980. While polyglycolic acid maintains its integrity in vivo for about 28 days, in certain surgical uses, for example, in the colon, the rate of healing is more rapid. Accordingly, the surgical support is no longer required after the wound healing period.

An implanted surgical element may require a relatively high initial tensile strength followed by relatively rapid loss of strength and/or disintegration rate. For example, in the gastrointestinal anastomosis device, a relatively high initial tensile strength is required but removal of the device should occur in about 8 to 15 days. Since the device does not absorb in that length of time, even though made of polyglycolic acid, it must be removed by other means, such as by passage through the body. This is achieved through disintegration and passage of device fragments.

As used in this application, a "structural surgical element" refers to a surgical element of bioabsorbable polymer which provides a support, holding or reinforcement function in the body which function is complete prior to absorption of the element as such so that the element desirably disintegrates into desired particles or fragments for removal or passage from the body.

SUMMARY OF THE INVENTION

Applicants have discovered that the physical properties of structural surgical elements which are made from bioabsorbable materials having a glycolic ester linkage can be controlled so that the rate of strength loss and degradation in vivo is altered to achieve disintegration without the need for waiting until the material is absorbed. This is achieved, according to the present invention, by a method of modifying the element through various chemical and/or physical treatments, or combinations thereof, with the result that bioabsorbable structural surgical elements are made more controllable in their strength loss and degradation pattern.

Therefore, an object of this invention is the provision of a method for modifying the physical properties of structural surgical elements made of bioabsorbable materials.

Another object of this invention is the provision of a method for controlling the in vivo loss of strength and degradation into fragments of structural surgical elements made of bioabsorbable methods.

A further object of this invention is the provision of a structural surgical element made of bioabsorbable material which degrades in vivo into fragments suitable for removal from or passage through the body prior to absorption of the material from which it is made.

The foregoing and other objects, features and advantages of this invention will be further apparent from the following description of preferred embodiments thereof.

DESCRIPTION OF THE PREFERRED EMBODIMENTS

The initial strength and in vivo strength properties of polyglycolic acid structural surgical elements can be modified by the use of various fillers, for example, barium sulfate, and various concentrations of fillers. These properties can also be changed by lowering the intrinsic viscosity of the polyglycolic acid, filled or unfilled. This is accomplished by treating the filled or unfilled polyglycolic acid with dilute or concentrated ammonia or by subjecting it to hydroyltic degradation, for example, by distilled water, boiling, soaking or steam treatment. Also, the polyglycolic acid can be subjected to repelletizing. A particularly advantageous method, and the preferred, is treating the polyglycolic acid structural surgical element with appropriate amounts of irradiation to control not only the initial strength but also the in vivo strength and particularly the degradation rate of properties such as strength.

Not only strength and degradation rate but also fracture properties, compression strength, elongation, elastic modulus, and/or creep properties of polyglycolic acid structural surgical elements can be affected, particularly by controlling the filler. Nevertheless the most significant advantage of the method of this invention is the control of the time of strength loss and degradation in vivo so that the element disintegrates and is passed out of the body as fragments or particles prior to the time that it would normally be completely absorbed. By using more than one treatment method the desired effects can be controlled further and various results achieved. For example, while irradiation will achieve the most desirable results with respect to strength retention control a combination of irradiation and use of filler can produce other advantages. The fragments of filled polyglycolic acid elements are relatively small, for example, on the order of magnitude of 1/16th of an inch. Also, physiological forces may tend to enhance the fracture pattern.

It will be seen that by use of the method of this invention, the physical properties of the structural surgical element of bioabsorbable material can be closely matched to the physiological requirements of the surgical procedure or repair. Thus, depending on the surgical need, a surgeon has available an element with a variable range of initial and in vivo physical properties. In particular, advantages are seen in specific surgical uses such as the gastrointestinal anastomosis device. For example, the in vivo strength can be maintained up to 14 days but modified for relatively high tensile strength in implant but rapid loss of strength for tissues which heal rapidly, as in the bowel. The device can be caused to break down into particles of suitably small size and softer particles upon degradation so as to be passed on the body without harm.

The invention will be further apparent from the following examples.

EXAMPLE 1

The following example relates to the preparation of polyglycolic acid (PGA), or polyglycolic acid filled with 20%, 22.5%, 25% and 40% barium sulfate. PGA in pellet form can be injection molded without preprocessing steps 1. to 3.

1. Material Preparations 1.1 Grinding—PGA in pellet form is ground into 2 mm particles. The ground PGA is then stored in plastic bags in a dry cabinet at 70 F with less than 50 ppm $H_2O$ until it is mixed with the $BaSO_4$.

1.2 Mixing—The ground PGA is mixed with $BaSO_4$ using conventional techniques for mixing powders.

1.3 Polymer Drying—After mixing, the polymer blend is vacuum dried by maintaining a temperature of 120° C. with a vacuum of less than 10 mmHg for six hours. Dry nitrogen at 10 SCFH is run through the polymer.

2. Melt Blending

Additional mixing of the PGA/$BaSO_4$ blend is accomplished by melt blending the polymer using conventional techniques at a temperature of 270° C. The resultant blended material is then cooled to ambient temperature under dry conditions of less than 50 ppm $H_2O$ for 4 hours. It has been found that melt blending at 240° C. is preferred.

3. Granulation

After the blended material is cooled to ambient temperature, it is granulated into less than 5 mm particles, redried and vacuumed sealed in cups.

4. Molding Conditions

The PGA or PGA/$BaSO_4$ blend is injection molded into bowel anastomosis rings using conventional molding techniques.

Typical molding conditions are:
   Temperature: 235° C.
   Pressure: 600–1000 psi
   Cycle Time: 1 min.
   Injection Time: 55 sec.
   Molding Time: 10–15 sec.

A cycle time of 32 seconds and injection time of 5 seconds together with a molding time, that is, mold cure time, of 25 seconds is also satisfactory.

5. Post Molding Treatments

The molded device is subjected to the following post treatment conditions.

5.1 Annealing—110° C. with a vacuum of less than 1 mm. of Hg for 3 hours.

5.2 Etching—Placed in boiling $H_2O$ for 30 minutes, cooled and then dried in anhydrous methanol for 2½ hours, followed by drying in a vacuum oven at 50° C. and less than 1 mm. of Hg for 30 minutes.

6. Sterilization

The packaged post treated device is subjected to a gas chamber sterilization employing a sterilant mixture containing ethylene oxide with a diluent such as Freon ®. A typical sterilization cycle is described below:

| | |
|---|---|
| Temperature | 30° C. |
| Pre-Vacuum | 26" of Hg |
| RH | 20% |
| Gas | EO/Freon in a 12/88 ratio |
| Pressure | 20 PSIG |
| EO Concentration | 11100 mg/L |
| Exposure | 7 hours |
| Post Vacuum | 26" of Hg |

EXAMPLE 2

Various samples of a bowel anastomosis ring were prepared using the mixtures of Example 1. The preparation of the bowel anastomosis ring is described in a patent application Ser. No. 287,500, filed July 27, 1981 which is a continuation-in-part application of Ser. No. 198,448 referenced above, filed in the names of A. L. Kaganov, T. G. Hardy and W. G. Pace. Those applications are incorporated herein by reference. The hydrolytic treatment was a 30 minute distilled water boil. All of the samples were 28 mm in diameter. The percent barium sulfate and implant subject were as follows:

| Sample No. | % $BaSO_4$ | Implant Subject |
|---|---|---|
| 1 | 22.5 | Beagle |
| 2 | 22.5 | " |
| 3 | 22.5 | " |
| 4 | 22.5 | " |
| 5 | 22.5 | " |
| 6 | 40 | " |
| 7 | 40 | Foxhound |
| 8 | 25 | " |

Procedure

Prior to anesthetic induction, the animals received an enema and routine preinduction sedication. Under aseptic conditions a low midline laparotomy was made. The descending colon was mobilized and the mesenteric blood vessels supplying a selected segment were doubly ligated and transected. Purse-string sutures were placed proximally and distally to the devascularized colon segment using two purse-string bowel clamps that had been appropriately placed. The colon segment between the clamps was resected flush with the clamps and the segment was discarded. For implantation of the bowel anastomosis ring, the proximal clamp was removed first and the colonic stoma triangulated, cleansed with warm saline and dilated. One ring of the bowel anastomosis ring was inserted into the proximal stoma and the purse-string suture tied to secure the colon to the bowel anastomosis struts. This procedure was then repeated to insert the other bowel anastomosis ring into the distal stoma. Care was taken to align the mesentery during the bowel anastomosis ring insertion procedures. The bowel anastomosis rings were closed (forced closer together) using finger pressure on the colon serosa. The anastomosis was inspected to insure adequate serosa to serosa approximation around the circumference of the bowel anastomosis ring. When necessary, stitches were taken to insure the adequacy of the purse-string suture and/or the approximation of the serosa to serosa union.

When the anastomoses were completed, the colons were replaced and the laparotomies closed in three layers. The dogs were returned to cages and treated with routine post-operative antibiotics. The Beagles were given milk only on the first and second post-operative days. From days 3 to 17, they were fed canned dog food mixed with milk. Water was available at all times. Fecal material were fluoroscoped daily, except weekends. All five Beagles were sacrificed on the 17th post-operative day and anastomotic healing assessed. The Foxhounds were fed intravenously for seven days post-operatively. Radiographs were made daily. Fecal material was examined when warranted.

Results

The 40% BaSO$_4$ filled bowel anastomosis ring implanted in the Beagle began to fragment between the 4th and 7the post-operative day and had been completely excreted by the 12th day. In the Foxhound, the 40% filled bowel anastomosis ring had been excreted by the 6th day.

The rings of the 22.5% and 25% BaSO$_4$ filled bowel anastomosis rings separated as early as the 6th post-operative day and began fragmenting between the 8th and 11th post-operative days. Bowel anastomosis ring fragments were found in the fecal material from day 8 through day 16. In no instance were bowel anastomosis ring fragments found in the colon in those animals sacrificed on day 17.

Gross examination of the Beagles at autopsy showed excellent serosal healing with a thin band of scar tissue formation. The mucosae of the anastomoses ranged from barely perceptible to moderately indurated and slightly hyperemic. Recovered bowel anastomosis ring fragments from all the samples were hard and very brittle. When pressed between the fingers, the fragments crumbled easily.

EXAMPLE 3

Molded, 12.5% barium sulfate filled high and low inherent viscosity polyglycolic acid bowel anastomosis ring devices, irradiated at 0, 2.5, 5, 7.5 and 10 Mrad were used for colocolostomies in 31 beagle dogs to determine the effect of inherent viscosity, mass and radiation on fragmentation time. Since molding and mechanical parameters of the devices were not optimized, all but two were fixed in the colon with two sutures through the colon wall and ring device eyelets. The devices in eight animals were expelled intact. The results from 23 dogs in which the devices fragmented indicated that less massive devices began to fragment earlier than more massive devices but that inherent viscosity did not have a significant effect on fragmentation time. However, irradiation of the device had a significant effect on the fragmentation time with devices irradiated at 5 to 10 Mrads fragmenting sooner than those not irradiated. These results suggest that there is little significant effect of molecular weight, based on inherent viscosity, on the degradation time.

EXAMPLE 4

The relationship between fragmentation time and filler content with boiling water treatment was evaluated using the bowel anastomosis ring device, implanted in dogs as essentially described above. The average fragmentation times are summarized in TABLE I:

TABLE I

| Percent BASO4 | Boiling Treatment | Average Fragmentation Time |
|---|---|---|
| 25% | 30 mins. | 9.67 ± 1.03 days |
| 40% | 30 mins. | 10.0 ± 1.73 days |
| 0% | 45 mins. | 9 days (1 data point) |
| 25% | 45 mins. | 8.00 ± 1.00 days |

The foregoing show that there is no significant relationship between the combination of filler content and boiling treatment on in vivo property retention.

EXAMPLE 5

The in vivo fragmentation time for two types of bowel anastomosis ring devices of 25% barium sulfate with polyglycolic acid were compared for different boiling treatments and tabulated. The results are set forth in TABLE II.

TABLE II

| Device Style | Boiling Treatment | Average Fragmentation Time |
|---|---|---|
| 6 Tab | 30 mins. | 9.67 ± 1.03 days |
| 6 Tab | 45 mins. | 8.00 ± 1.00 days |
| 4 Tab | 0 mins. (as molded) | 16.17 ± 1.33 days |
| 4 Tab | 30 mins. | 11.4 ± 1.57 days |

The above show a much stronger relationship between boiling treatment time and fragmentation time. Boiling does more than affect molecular weight. It is theorized that selective changes in amorphous areas occur.

EXAMPLE 6

The effect of irradiation on a 12.5% barium sulfate filled polyglycolic acid bowel anastomosis ring device was determined using implantation in dogs as described above. The tabulation of the in vivo data using irradiation levels of 0, 5, 7.5 and 10 Mrads was subject to regression analysis with the result that fragmentation time was found to be 14.2-(0.322 times the irradiation dosage). This indicates that there is a trend of decreasing fragmentation time with increasing radiation level for this system.

The effect of the treatment methods of this invention in vivo property retention were compared in a carefully controlled study utilizing polyglycolic acid injection molded rods implanted in rabbits and evaluated at intervals by mechanical testing of measurement of the flexual properties in 3-point bending promptly after recovery from the rabbits. This is described in the following examples.

EXAMPLE 7

Lots of 0, 12.5 and 25% barium sulfate filled polyglycolic acid were injection molded into circular cross-section rods 15 mm. long by 2.25 mm. in diameter with a small pin hole at each end for immobilization during implant by suturing in place. Approximately 400 rods of each material were injection molded. Each set of the three filler content rods were separately xylene washed with three contacts of 5 minutes each and vacuum dried over night at room temperature. Following annealing under a vacuum at a 110° C. for three hours each set was divided into five groups and each rod individually packaged with a foam insert in an aluminum foil envelope. The treatments were as follows:

A. Rods were subjected to a standard open cycle ethylene oxide gas sterilization, vacuum dried and sealed in foil, TYVEK ® outers were sealed and the package subjected to standard closed cycle ethylene oxide gas sterilization.

B. Rods were placed in boiling deionized water for 30 minutes, strained, soaked for five contacts of 30 minutes each contact in anhydrous methanol with agitation, overnight vacuum dried at room temperature, followed by the ethylene oxide sterilization procedure of A; above.

C. After sealing in foil and TYVEK ® outers, rods received Cobalt-60 irradiation treatment at 0.5 Mrads per hour dosage rate at the following amounts: 2.5 Mrad (actual equal to 2.53), 5.0 Mrad (actual equal to 5.09) and 10 Mrad (actual equal to 10.36). Dosage rates greater than the accepted standards for sterilization, 1 Mrad in Europe and 2.5 Mrads in the United States, were used.

The rod samples were implanted subcutaneously through a ventral midline incision in rabbits and imobilized using TI-CRON ® 6/0 sutures through the pin holes in each end of the rods. A total of 10 rods was implanted in each animal. Randomization was accomplished by implanting two rods in each of five animals for any set and implant interval. Mechanical testing consisted of measurement of the flexual properties in 3 point bending of each rod promptly after recovery from the rabbits. The flexural strength, strain and modulus values expressed as percentage retention of baseline properties are presented in TABLES III, IV and V. In the tables, the day refers to the number of days implanted in the rabbits, BL refers to the non-implant or baseline while E is the flexural modulus, S is the flexural strength, psi, ultimate and r is the flexural strain, %, ultimate. For each filler content/process condition and interval, a total of 10 data points were collected in obtaining the property average and standard deviation unless otherwise indicated. In some cases less than 10 data points were available due to either breakage of samples in the rabbit prior to recovery or breakage in attempts to fixture samples for mechanical testing. Comparisons here are based on flexural strength considerations.

TABLE III

| | Treatment Method A-EtO | | | | | | | | |
|---|---|---|---|---|---|---|---|---|---|
| | 0% $BaSO_4$ | | | 12.5% $BaSO_4$ | | | 25% $BaSO_4$ | | |
| Day | E | S | r | E | S | r | E | S | r |
| BL: | 467,000 ± 25,500 | 57,300 ± 2,650 | 34.5 ± 3.98 | 441,000 ± 11,400 | 42,300 ± 1,900 | 10.8 ± 0.69 | 468,000 ± 28,300 | 33,700 ± 1,460 | 8.14 ± 0.70 |
| 7: | 72.6% ± 6.7% | 36.1% ± 8.4% | 21.4% ± 4.1% | 82.3% ± 2.2% | 71.4% ± 18.0% | 96.3% ± 34.0 | 70.7% ± 5.1% | 56.4% ± 11.9% | 82.7% ± 25.3% |
| 14: | 22.9% ± 4.78% | 16.6% ± 3.89% | 55.1% ± 7.59% | 29.7% ± 10.8% | 28.6% ± 11.1% | 156% ± 25% | 23.3% ± 9.74% | 26.0% ± 7.69% | 179% ± 18.2% |
| 21: | 7.90% ± 2.63% | 3.84% ± 2.69% | 28.3% ± 13.6% | 10.6% ± 3.8% | 9.13% ± 3.62% | 119% ± 38.2% | 5.66% ± 1.38% | 3.00% ± 1.71% | 56.1% ± 23.8% |

TABLE IV

| | Treatment Method B - $H_2O$ Boil & EtO | | | | | | | | |
|---|---|---|---|---|---|---|---|---|---|
| | 0% $BaSO_4$ | | | 12.5% $BaSO_4$ | | | 25% $BaSO_4$ | | |
| Day | E | S | r | E | S | r | E | S | r |
| BL: | 459,000 ± 28,600 | 36,300 ± 7,490 | 9.54 ± 3.82 | 449,000 ± 18,400 | 30,200 ± 2,220 | 7.46 ± 0.46 | 480,000 ± 33,700 | 26,500 ± 1,410 | 5.91 ± 0.32 |
| 3: | 72.5% ± 5.8% | 80.2% ± 16.2% | 110% ± 24.6% | 75.5% ± 5.5% | 87.1% ± 22.8% | 123% ± 48.1% | 65.4% ± 13.1% | 72.1% ± 18.0% | 113% ± 25.9% |
| 7: | 39.0% ± 7.6% | 35.0% ± 10.4% | 172% ± 60% | 51.7% ± 7.6% | 58.3% ± 3.1% | 142% ± 22.3% | 39.6% ± 7.9% | 46.4% ± 6.7% | 195% ± 64.0% |
| 14: | 9.35% ± 4.62% | 5.34% ± 3.03% | 83.4% ± 42.4% | 13.9% ± 4.5% | 15.1% ± 5.0% | 181% ± 70.1% | 11.0% ± 2.21% | 10.3% ± 2.54% | 145% ± 52.8% |

TABLE V

| | Treatment Method C - Irradiation | | | | | | | | |
|---|---|---|---|---|---|---|---|---|---|
| | 0% $BaSO_4$ | | | 12.5% $BaSO_4$ | | | 25% $BaSO_4$ | | |
| Day | E | S | r | E | S | r | E | S | r |
| | | | | 2.5 Mrad | | | | | |

TABLE V-continued

| | Treatment Method C - Irradiation | | | | | | | | |
|---|---|---|---|---|---|---|---|---|---|
| | 0% BaSO$_4$ | | | 12.5% BaSO$_4$ | | | 25% BaSO$_4$ | | |
| Day | E | S | r | E | S | r | E | S | r |
| BL: | 436,00 ± 15,400 | 52,700 ± 3,080 | 28.9 ± 7.74 | 430,000 ± 19,200 | 40,800 ± 1,340 | 11.1 ± 0.59 | 454,000 ± 31,200 | 35,900 ± 2,150 | 9.02 ± 0.54 |
| 7: | 39.2% ± 6.2% | 29.0% ± 2.5% | 54.0% ± 7.3% | 50.9% ± 6.2% | 39.0% ± 6.1% | 87.9% ± 20.7% | 40.7% ± 7.2% | 34.0% ± 3.8% | 107% ± 22.7% |
| 14: | 8.9% ± 1.9% | 4.3% ± 1.1% (n = 8) | 31.7% ± 9.8% | 12.9% ± 2.1% | 7.6% ± 2.3% | 74.1% ± 25.8% | 9.9% ± 2.5% | 6.4% ± 2.7% (n = 9) | 73.2% ± 17.3% |
| 21: | 0.67% | 0.44% (n = 1) | 28.9% | 3.81% ± 1.43% | 1.11% ± 0.87% (n = 8) | 30.0% ± 9.10% | 3.52% ± 2.49% | 0.83% ± 1.08% (n = 8) | 33.6% ± 16.9% |
| | | | | 5.0 Mrad | | | | | |
| BL: | 447,000 ± 28,000 | 49,000 ± 1,730 | 22.7 ± 2.66 | 426,000 ± 23,500 | 37,400 ± 1,330 | 9.91 ± 0.86 | 462,000 ± 27,500 | 34,300 ± 1,590 | 8.39 ± 0.70 |
| 3: | 74.3% ± 6.8% | 50.6% ± 15.9% | 36.9% ± 9.9% | 71.1% ± 7.7% | 81.6% ± 10.5% | 120% ± 2.2% | 67.3% ± 10.8% | 58.6% ± 11.7% | 85.7% ± 11.8% |
| 7: (n = 9) | 38.7% ± 5.9% | 25.5% ± 2.2% | 59.5% ± 8.2% | 44.8% ± 6.9% | 36.6% ± 4.0% | 105% ± 17.8% | 34.4% ± 9.6% | 28.5% ± 2.4% | 110% ± 28.4% |
| 14: (n = 7) | 7.5% ± 2.7% | 2.4% ± 1.2% | 20.9% ± 8.6% | 11.5% ± 1.86% | 4.87% ± 2.91% | 52.4% ± 32.4% | 8.25% ± 2.90% | 2.97% ± 1.33% | 45.8% ± 20.7% |
| | | | | 10.0 Mrad | | | | | |
| BL: | 427,000 ± 30,500 | 47,000 ± 2,330 | 14.7 ± 1.63 | 432,000 ± 8,050 | 36,100 ± 1,690 | 9.44 ± 0.77 | 458,000 ± 35,500 | 31,100 ± 2,370 | 7.24 ± 0.49 |
| 3: | 76.8% ± 4.8% | 29.4% ± 5.1% | 32.8% ± 4.7% | 72.2% ± 5.4% | 43.8% ± 9.3% | 59.3% ± 12.0% | 62.7% ± 8.1% | 40.5% ± 5.8% | 71.3% ± 15.9% |
| 7: | 31.9% ± 11.6% | 20.7% ± 3.9% | 81.6% ± 18.2% | 32.4% ± 4.6% | 28.8% ± 2.7% | 111% ± 14.6% | 32.5% ± 7.8% | 23.3% ± 3.2% | 119% ± 27.3% |
| 14: | 6.42% ± 2.95% | 1.40% ± 1.30% | 21.9% ± 10.8% | 7.36% ± 2.87% | 2.45% ± 2.20% | 36.3% ± 31.17% | 4.34% ± 2.45% | 1.46% ± 1.25% (n = 9) | 37.6% ± 24.0% |

Several conclusions can be drawn from the results set forth in TABLES III, IV and V. As to the effect of boiling water treatment, it can be seen that the 30 minute water boiled samples exhibited consistently lower strengths than the control at each of the implant intervals as well as at the baseline. The same relationship held for percent retention of initial strength in general with the exception of the 0 percent filler at the 7 day implant interval. It can therefore be concluded that boiling water treatment reduces both the in vivo strength as well as percent retention of strength of the polyglycolic acid structural surgical elements.

In vivo strengths exhibited considerable variation with filler content and no significant trends were apparent although baseline strengths were consistantly ranked as decreasing with increasing filler content. Accordingly, it can be concluded that increasing the barium sulfate filler content has the effect of reducing the initial strength but little effect on the strength end point or life of the structural surgical element.

Cobalt-60 irradiation treatment resulted in decreasing strength and percentage retention of initial strength with increasing dosage level. However, the initial strength reduction was not as great as that with the other treatments although the satisfactory end point was reached, that is percentage reduction in strength in vivo. Similar in vivo strength and retention of strength was exhibited by samples treated with the Cobalt-60 gamma radiation at 2.5 or 5.0 Mrad as compared with the 30 minute water boil treatment. The irradiated samples exhibited higher baseline strengths and it has been found that they provide adequate storage stability.

The most satisfactory means for decreasing in vivo strength retention of polyglycolic acid structural surgical elements as compared to conventional ethylene oxide sterilized elements is the Cobalt-60 gamma radiation treatment. These results are surprising and unpredictable since it is known that polyglycolic acid differs in its response to irradiation from other polymers. Moreover, the boiling water treatment while reducing strength does not provide for stability whereas the irradiation treatment does.

Although the filler utilized was barium sulfate, those skilled in the art will recognize that the filler can comprise calcium carbonate, tricalcium phosphate, magnesium oxide, glass spheres and non-polyglycolic acid fibers. Also, those skilled in the art will recognize that the polymer may be a homopolymer of glycolide or a copolymer, one of the monomers of which is glycolide. Where the polymer is a copolymer and one of the monomers is glycolide, the other monomer may be obtained from the group consisting of alactide, lactone, oxalate or carbonate. The lactide may be the species lactide; the lactone, epsilon-caprolactone; and the oxalate, ethylene oxalate. The carbonate may be trimethylene carbonate. Also, when the polymer is a copolymer and one of the monomers is glycolide, the other monomer may be 1,4-dioxanone.

Although the invention has been shown with particular reference to the bowel anastomosis device, it will be recognized that it is applicable to other structural surgical elements of polyglycolic acid where it is desired that the element disintegrate, that is degrade into fragments prior to the time that it would be absorbed. Thus, the invention is applicable to polyglycolic acid prostheses such as surgical clips and surgical staples as well as tubular supports, implants and stenotic devices and other surgical elements in which it may be desirable to have a loss of strength at a certain time in the healing process prior to absorption of the polymer itself. Those skilled in the art will also recognize, as the data indicates, that varying certain treatment parameters, such as irradiation levels and dosage rates may vary the effect on in vivo retention of properties.

We claim:

1. A method of modifying a structural surgical element made from a bioabsorbable polymer having a glycolic ester linkage to controllably effect a rapid loss of its in vivo tensile strength, said element selected from the group consisting of a tubular support, tubular implant, tubular stenotic device and ring device, comprising subjecting the element to irradiation treatment in a dosage amount greater than that required for sterilization and in a controllable manner such that the time required for the element to undergo in vivo degradation into fragments, capable of being removed from or passed out of the body without absorption, is from about 8 to 15 days.

2. A method of modifying a structural surgical element as claimed in claim 1 wherein the irradiation dosage is up to about 10 Mrads.

3. A method of modifying a structural surgical element as claimed in claim 1 or 2 wherein the in vivo degradation into fragments is brought about by a loss of in vivo strength of the element which has been accelerated by the irradiation treatment without significant loss of strength of the element, compared to no irradiation treatment, prior to in vivo implantation.

* * * * *